(12) United States Patent  (10) Patent No.: US 9,271,769 B2
Batsch et al.  (45) Date of Patent: Mar. 1, 2016

(54) BONE PLATE AND FIXATION SYSTEM COMPRISING A BONE PLATE

(71) Applicant: aap Implantate AG, Berlin (DE)

(72) Inventors: Thomas Batsch, Berlin (DE); Thomas Paulin, Wilhelmshorst OT Michendorf (DE); Hans-Joachim Fischer, Berlin (DE); Bruke Seyoum Alemu, Berlin (DE)

(73) Assignee: aap Implantate AG (DE)

( * ) Notice: Subject to any disclaimer, the term of this patent is extended or adjusted under 35 U.S.C. 154(b) by 0 days.

(21) Appl. No.: 14/510,499

(22) Filed: Oct. 9, 2014

(65) Prior Publication Data

US 2015/0094775 A1  Apr. 2, 2015

Related U.S. Application Data

(63) Continuation of application No. 13/805,444, filed as application No. PCT/EP2011/003111 on Jun. 24, 2011, now Pat. No. 8,888,825.

(60) Provisional application No. 61/358,171, filed on Jun. 24, 2010.

(30) Foreign Application Priority Data

Jun. 24, 2010 (DE) .................. 10 2010 025 001

(51) Int. Cl.
*A61B 17/80* (2006.01)
*A61B 17/86* (2006.01)
*A61B 17/00* (2006.01)

(52) U.S. Cl.
CPC ......... *A61B 17/8014* (2013.01); *A61B 17/8047* (2013.01); *A61B 17/8057* (2013.01); *A61B 17/8605* (2013.01); *A61B 2017/00004* (2013.01)

(58) Field of Classification Search
CPC ............... A61B 17/80; A61B 17/8057; A61B 17/8014; A61B 17/8047
USPC .................................................. 606/280–331
See application file for complete search history.

(56) References Cited

U.S. PATENT DOCUMENTS 3,779,240 A * 12/1973 Kondo .......................... 606/282
4,408,601 A * 10/1983 Wenk ............................ 606/282

(Continued)

FOREIGN PATENT DOCUMENTS

DE  19858889 A1  6/2000
EP  0760632 B1  10/1996

(Continued)

OTHER PUBLICATIONS

Yolaine Cussac, "International Patent Application No. PCT/EP2011/003111 International Preliminary Report on Patentability", Jan. 10, 2013, Publisher: PCT, Published in: EP.

(Continued)

*Primary Examiner* — Christopher Beccia
(74) *Attorney, Agent, or Firm* — Kaplan Breyer Schwarz & Ottesen, LLP (57) ABSTRACT

A bone plate and to a fixation system comprising two types of bone screws. The bone plate has two intersecting stepped round holes which are different in size and in the upper regions of which a circumferential rib extends. The upper region of the smaller round hole is designed to slidably guide a bone screw having a partially spherical heads and a screw having a thread or conical head. The lower region of the larger round hole is used to support a conical head.

18 Claims, 8 Drawing Sheets

(56) References Cited

U.S. PATENT DOCUMENTS

| | | | |
|---|---|---|---|
| 6,719,759 B2 * | 4/2004 | Wagner et al. | 606/282 |
| 2005/0010226 A1 * | 1/2005 | Grady et al. | 606/69 |
| 2008/0051786 A1 * | 2/2008 | Jensen | 606/61 |
| 2008/0234749 A1 * | 9/2008 | Forstein | 606/291 |

FOREIGN PATENT DOCUMENTS

| | | |
|---|---|---|
| EP | 1255498 B1 | 8/2001 |
| EP | 1158915 A1 | 12/2001 |
| EP | 1158916 B1 | 12/2001 |
| EP | 1649819 A1 | 4/2006 |
| EP | 1949866 A2 | 7/2008 |
| EP | 2016918 A1 | 1/2009 |
| FR | 2880929 A1 | 7/2006 |
| WO | 2004084701 A2 | 10/2004 |

OTHER PUBLICATIONS

Marios Kakoullis, "International Application No. PCT/EP2011-003111 International Search Report", Sep. 11, 2011, Publisher: PCT, Published in: EP.

* cited by examiner

BONE PLATE AND FIXATION SYSTEM COMPRISING A BONE PLATE

CROSS-REFERENCE TO RELATED APPLICATION(S)

This application is a Continuation of U.S. patent application Ser. No. 13/805,444, incorporated herein by reference.

U.S. patent application Ser. No. 13/805,444 is a 35 U.S.C. 371 filing of International Application Number PCT/EP2011/003111, filed on Jun. 24, 2011, incorporated herein by reference.

International Application Number PCT/EP2011/003111 in turn claims priority to U.S. Provisional Application No. 61/358,171 and German Patent Application Number 10-2010-025-001.5, filed on Jun. 24, 2010, incorporated herein by reference.

FIELD OF THE INVENTION

The invention relates to a bone plate with several holes arranged in the direction of the plate longitudinal axis, for accepting bone screws, as well as a fixation system for bones, having a bone plate.

BACKGROUND OF THE INVENTION

With a known bone plate of this kind (EP 0760632 B1), the holes are all around spherically formed towards the upper side of the bone plate, in order to be able to support a bone screw with a head having a spherical lower side, in different angular positions. At the plate lower side, adjacent to the bone, the holes have a region of smaller diameter with partial thread in order to be able also to accept a bone screw with cylindrical threaded head which screw shall be inserted, vertically to the plate plane.

With a further bone plate of the specified kind (EP 1158915 B1, and EP 1198916 B1), elongated holes with an internal thread are available which thread extends from the upper side to the lower side of the bone plate, at one end of the elongated hole, and has a peripheral or central angle in the range from 190 to 280°. The internal thread extends over the whole depth of the elongated hole, tapers towards the lower side of the bone plate, and has a cone angle in the range from 5 to 20°.

With a further known bone plate (EP 1255498 B1), elongated holes are provided in the bone plate which holes may be formed oval, ellipsoidal, or rectangular, or may have a combination of such forms. Only circular holes are explicitly not covered by this definition of an elongated hole. The elongated hole is combined with a circular hole, and the latter is provided with a three-dimensional structuring which is available in the form of an internal thread, or a peripheral plate or lip. A conical internal thread is shown which extends from the upper side to the lower side of the bone plate, and has a peripheral or central angle in the range from 190 to 280°.

A fixation system for bones, having a bone plate is known from DE 19858889 A1 which system has elongated holes which have lugs closely to their lower sides adjacent to the bone. The lugs extend in the lower part of the elongated hole, in parallel to the plate plane. There are bearing surfaces for spherical heads of the bone screws, towards the upper side of the bone plate. For cooperating with the lugs of the bone plates, the bone screw has a short piece of thread, below the spherical head which thread is able to deform the lugs in the elongated hole, and to adapt. It is thereby possible to screw the bone screw in different angle positions with respect to the axis of the passage holes.

SUMMARY OF THE INVENTION

The invention is based on the object to provide a bone plate with which various bone screws—such with conical bearing surfaces, and such with spherical bearing surfaces—may be used, in order to meet the different requirements, when fixing a fractured or damaged bone. In particular, bone fragments may be able to be shifted relatively to each other during fixation.

The bone plate in detail comprises a preferably lengthy plate body of tissue-compatible, rigid material, the plate body defining an upper side, a lower side, and a longitudinal axis. Transversely to the plate plane, shaped hole are provided which consist of a first, larger round hole, and a second, smaller round hole, wherein the round holes intersect while forming edges between which a passage for the screw shaft of a bone screw is formed. A circumferential radial rib is provided around both round holes which rib starts at the hole wall, and extends in a plane towards the round hole centre. It is within the scope of the invention that this rib extends in a plane, and is not provided with a lead, like with a thread. In case of embodiments with a circumferentially closed or annularly closed rib, an improved strength, in particularly a higher rigidity may be provided, that is principally not possible with a thread.

A bone screw having a thread at the screw head may rest on the rib of the smaller round hole, and makes an engagement for the rib of the larger round hole possible, whereby mutual clamping takes place.

Within the meaning of the invention, this clamping may also cause an elastic deformation which, however, does not essentially leave a permanent, deformed part after separating the bone screw from the bone plate. This means that this deformation does not also still comprises a plastic deformation, in excess of the purely elastic part. After separating the bone screw from the plate, no ridges or grooves may therefore be seen at the bone screw, or also at the bone plate. If surface changes are generated by improper handling, these changes typically are not present as grooves, channels, or ridges, but rather as laminar rubs.

According to preferred embodiments, the first, larger round hole has three sections, namely an upper, rounded flute shaped section above the circumferential rib, a central rounded flute shaped section below the circumferential rib, and a lower, lower truncated cone shaped section tapering to the lower side of the plate body, and having a largest diameter which is smaller than the diameter of the upper or central section. The smaller round hole comprises an upper section having a sloping transitional region towards the plate surface, further a central section below the plane of the circumferential rib, having a sloping rounded surface, and a lower, cylindrical or conical section having a diameter which is smaller than the diameter of the upper or central section.

With all embodiments, bone screws having a head may be used which head is provided with a screw thread in its upper region, and with a conical bearing surface in its lower region, and indeed in this way that, when inserting vertically into a bone, shifting the head relatively to the shaped hole stakes place, in such a way that bone fragments may be drawn near to each other, when fixing. The new bone plate, however, also allows using bone screws with spherical bearing surfaces at the lower side of the screw head. Such spherical head screws may be screwed in, in an angle to the bone plate, as it is necessary, sometimes.

Further details of the invention result from the description of the shown embodiments and the attached claims.

DETAILED DESCRIPTION

In the following detailed description of preferred embodiments, same reference signs essentially describe same parts in or at these embodiments, for the sake of clarity.

The figures show the part of a bone plate comprising a preferably lengthy plate body 1 made of tissue compatible, rigid material, and in which body a row of shaped holes is placed of which a shaped hole 2 is shown. The plate body 1 may also be formed, besides lengthy, oval, round, or polygonal, or its form may be fitted to the respective use.

Metals and their alloys are considered to be tissue compatible material, as they are usually used form producing implants. Preferred metals comprise each kind of titanium, preferably also its alloys TiAl6V4, and TiCp. Also steels such as implant steels, for example the alloy 1.4441 are preferably useable.

A further material class for this purpose also comprises absorbable materials, like magnesium, or absorbable synthetic material, like PLA. PLA is a bio-compatible and absorbable synthetic material made of lactic acid molecules chemically bond to each other which material may also be used like other absorbable synthetic materials.

A bone plate is considered to be rigid, if the plate structurally provides the rigidity necessary for its intended use and operation purpose. Depending on the used tissue compatible material, this may be ensured by the thickness and the width of the plate, and usually is within the scope of activities of a person skilled in the art.

Bone plates for small and less stressed body parts such as hand bones and foot bones for example are thinner and often less wider than bone plates of the larger and stronger stresses parts such as parts of the shank and of the thigh.

The bone plate has an upper side 11 and a lower side 12 which usually extend in parallel to the plate plane, wherein the lower side 12 is adjacent to the bone to be fixed. The shaped holes 2 are strung along the longitudinal axis of the lengthy plate body 1, and consist of two stagely formed round holes, 21 and 22, extending transversely to the plate plane, and whose axes 21a, 22a intersect the longitudinal axis of the bone plate. The smallest diameter of the first round hole 21 is greater than the smallest diameter of the second round hole 22, and the distance of the two axes 21a and 22a from each other is smaller than the smallest diameter of the first round hole. Edges 23, 24 result from the intersection of the holes 21, 22 which edges delimit the regions of the round holes from each other, and leave open a passage for the relatively thin screw shaft of a bone screw, if this screw extends into the other round hole, in case of inclination of a bone screw. The peripheral angles of the wall soffits of the round holes 21, 22 are 250° of the larger hole, and 220° of the smaller hole. Variations of 10° smaller and 20° greater are possible.

Due to the stage form of the round holes 21, 22, one may distinguish an upper region 25, and a lower region 26 of the round hole 21, and an upper region 27, as well as a lower region 28 of the round hole 22.

The upper regions 25 and 27 are formed bowl-like with extended radial range, while the lower regions 26 and 28 form generated surfaces with straight surface lines. The upper regions 25 and 27 have larger diameters with respect to the lower regions 26 and 28. The lower region 26 forms a truncated cone shaped section which tapers towards the lower side of the plate body 1. The lower region 28 is formed cylindrical, but it may also be formed truncated cone shaped.

While the two upper regions 25 and 27 of the two round holes 21, 22 are in total formed bowl-like, a radial rib 33 extends, starting at the hole walls, in a plane around the shaped hole 2. Rib 33 is formed as a circumferential web, and has a wedge-shaped cross section which tapers towards the centre of the respective round hole. The rib 33 seems to be similar to an "eight", in top view.

Figure 1:
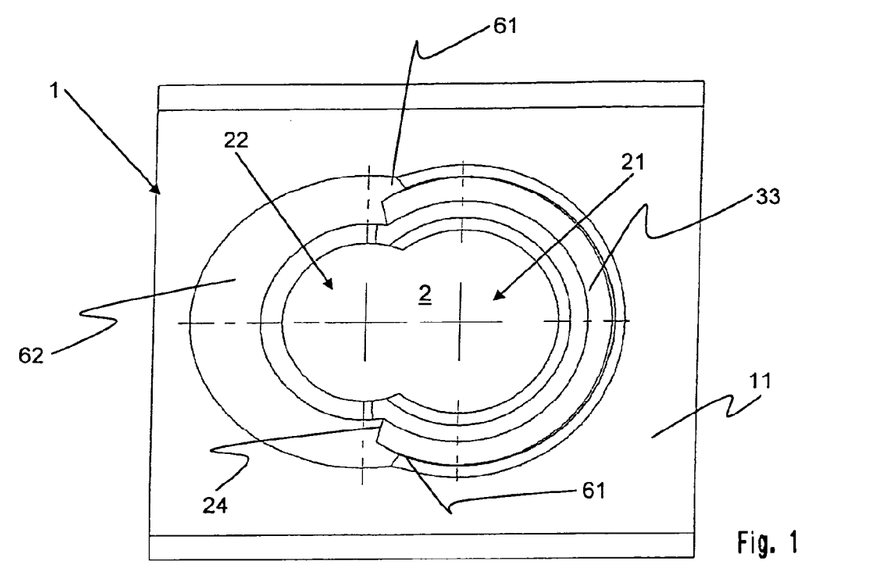
FIG. 1 is a top view onto a shaped hole in a bone plate.
Figure 2:
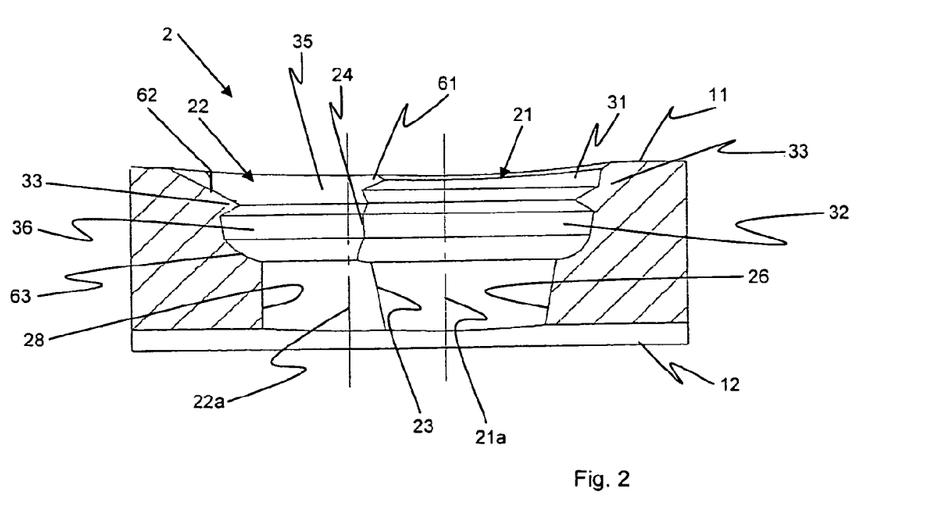
FIG. 2 is a sectional view of the shaped hole.
Figure 3:
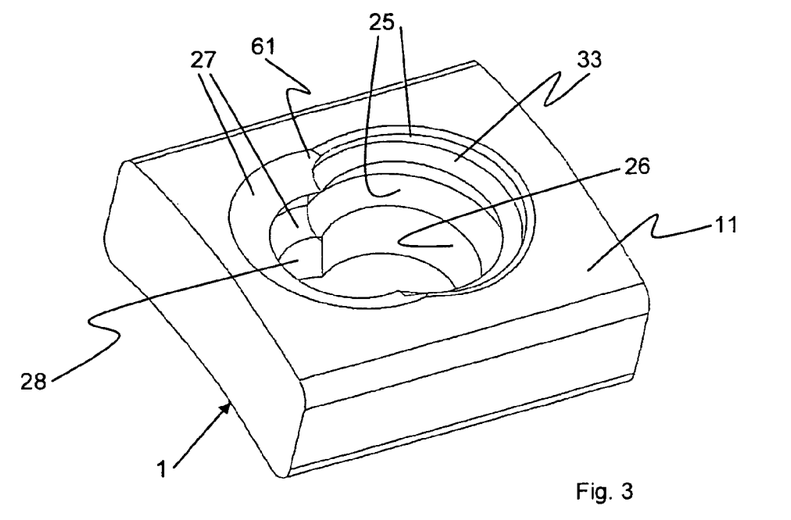
FIG. 3 is a perspective drawing of the shaped hole.

While the rib 33 may uniformly extend around, a ridge 61 is arranged for the rib part fixed to the larger round hole in parallel to the plane of the lug 33 at the outer edge of the larger round hole by what an edge 24 towards the second round 22 hole is formed. Starting from the longitudinal axis of the plate body 1, the height of the lug 61 increases towards the edge of the plate body 1 what results best from comparing FIG. 4 with FIG. 3. Between the lug 61 and the rib 33, a guidance is formed which favours the engagement of the thread 41 of the head screw 40.

Each of the two round holes 21, 22 is divided into three sections: Above the lug 33, the larger round hole 21 has an upper rounded flute shaped section 31 with or also without ridge 61. Below the rib 33, a central, round flute shaped section 36, and a lower, truncated cone shaped or conical section 26 are provided. The smaller round hole 22 comprises an upper section 35 with a leading-in slope 62, a central section 36 having a sloping rounded surface 63 below the plane of the rib 33, and a lower section 28 which is preferably formed cylindrical, but may also be conical.

The bone plate is formed for cooperating with at least two kinds of bone screws.

The one kind has a bone screw head with a partially spherical lower side, and may rest on the sloping rounded surface 63 with the head lower side. Thereby, an inclination of the screw axis with respect to the plate plane also is possible, and indeed in longitudinal direction as well as (in a minor degree) transversely to the bone plate. This is made possible by the distance of the edges 23 from each other which distance is selected, accordingly to the intended purpose.

Figure 4:
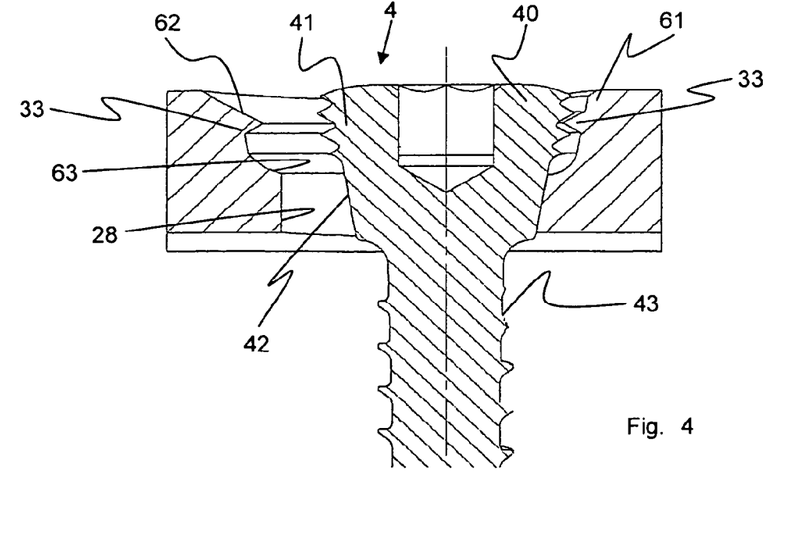
FIG. 4 shows a bone screw engaging a shaped hole.
Figure 5:
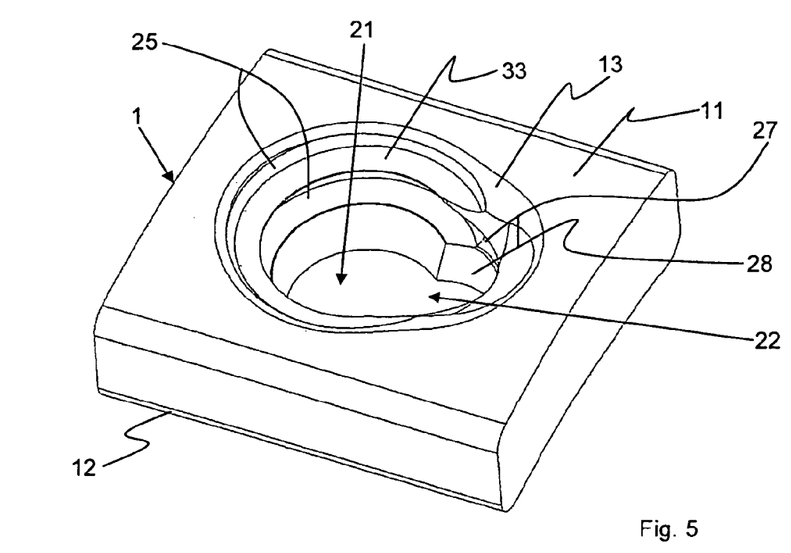
FIG. 5 shows a second embodiment of a bone plate in perspective drawing.
Figure 6:
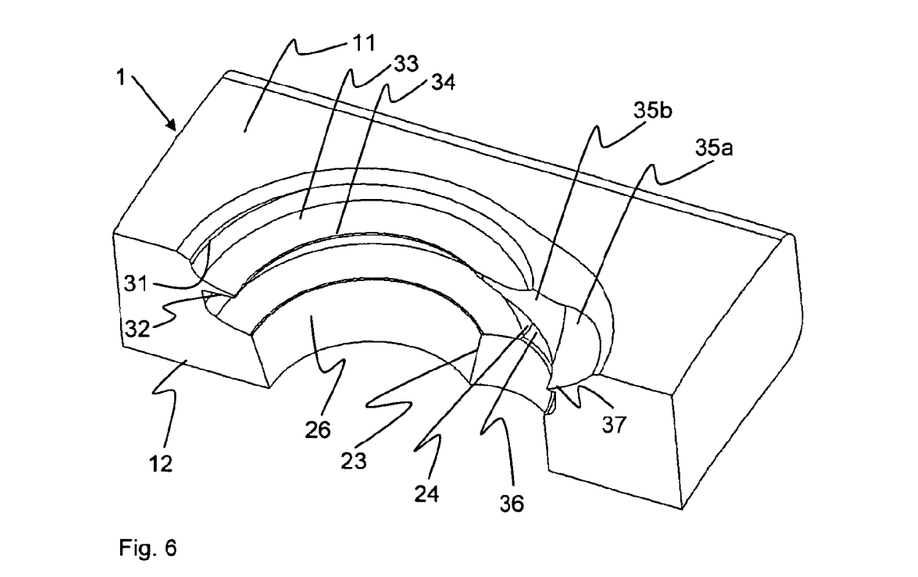
FIG. 6 is a sectional view of the shaped hole.
Figure 7:
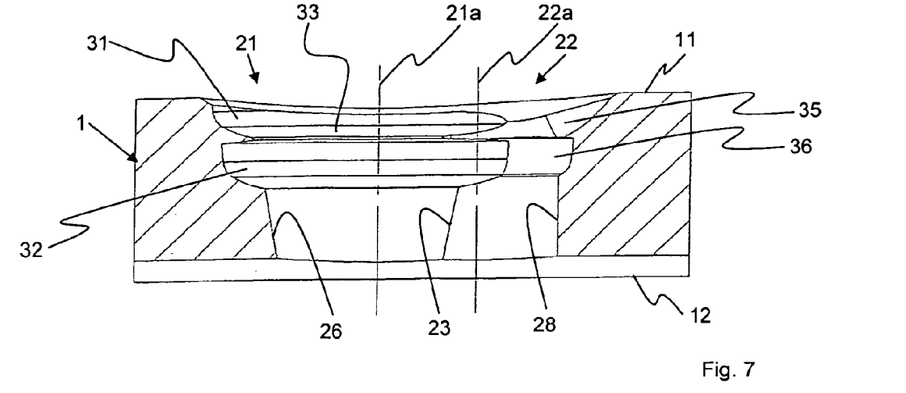
FIG. 7 is a lateral view of the shaped hole.
Figure 8:
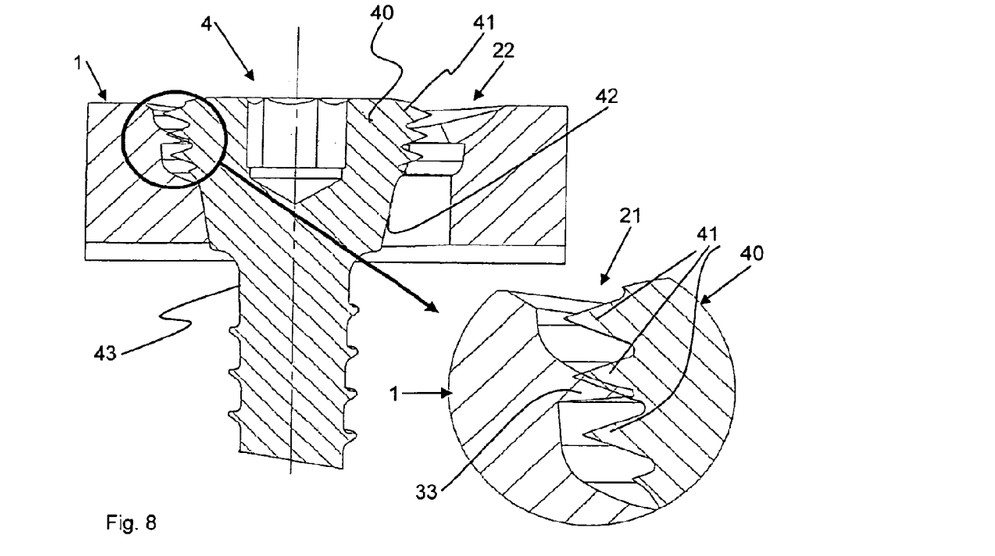
FIG. 8 shows a bone screw engaging a shaped hole, together with an enlarged sectional view.

A further kind of usable bone screw 4 is shown in FIG. 4. This bone screw 4 has a screw head 40 with interior engagement and with external thread 41 at the upper end, as well as a conical support plane 42 at the lower end. The cone inclination of the support plane corresponds to the cone inclination of the lower region 26 of the larger round hole 21.

The cone inclination of the lower region 26 of the larger round hole 21, as well as the cone inclination of the conical supporting plane at the lower end of the screw head 40 of the bone screw 4 has an angle in the range of 3 to 30°, relatively to the longitudinal of the symmetry axis, or of the round hole, each. This cone angle preferably is in a range of 5 to 20°, and most preferably in a range from 8 to 12°. A mostly preferred design has very proven of value, with a cone angle of about 10°, with high values of endurance strength, and a good detachability of the connection between the bone screw and the bone plate.

In an angle range from about 8 to 12°, very good stability values are provided against tilting of the bone screw relatively to the bone plate, while simultaneously by providing only moderate self-locking.

The external thread 41 may be cylindrical, but a conical thread is preferred. The screw head 40 is followed by a screw shaft 42 which is intended for being fastened in a bone element to be fixed. The circumferential rib 33 extends in a plane, preferably in parallel to the plate plane, while the thread 41 extends along screw surfaces which extend transversely opposite to the plane of the radial rib 33, and indeed also, if the bone screw 4 is brought into engagement with in parallel, or unidirectionally with the axis 21*a* of the round hole 21. When doing so, the clamping takes place between the threads 41 and the rib 33. In this regard, the ridge 61 is useful, because it offers a counter bearing for the thread of the screw head, and thereby provides a defined clamping with a defined self-locking effect.

In connection with the shown bone plate, the bone screw 4 may be used for approaching mutually, and for pressing together bone fragments. To this end, the bone screw 4 is placed with its axis in parallel to the axis 22*a* of the round hole 22. As soon as the lower edge of the conical supporting surface 42 reaches the leading-in slope 62 of the smaller round hole 22, a lateral force onto the screw head 40 is effected, while screwing-in the screw what causes a displacement of the bone fragment to be fixed, relatively to the bone plate. If a bone fragment is thus already being fixedly connected with the bone plate, this bone fragment is shifted against the bone fragment to be fixed, as it is wanted.

It is pointed out that due to the large peripheral angle of the cone surface of the lower region 26 which angle is in the range from 250 to 290°, a sufficiently strong connection between the plate body 1 and the bone screw 4 is effected, in case of a seized screw head 40, because the circumferential rib 33 generates enough elastic tension force after clamping the screw threads 43 for keeping the conical surfaces being pressed onto each other at 25 and 42.

By means of FIGS. 5-8, a further embodiment of the bone plate is shown, wherein the same reference signs are used for corresponding parts.

The main difference is the design of the circumferential, radial rib 33. This rib is partially cut off in the region of the smaller round hole 22, in order to provide a sloped, rounded sliding surface 35*a*, and a transitional surface 35*b* which is useful for guiding the head of a bone screw with partial spherical lower side of the head. A residual rib 37 is formed which increases to the full dimension of the rib 33, in the region of the larger round hole 21. The remaining border edge 34 extends by less than 180°, and so allows the lateral insertion of bone screws from the smaller round hole 22 into the larger round hole 21.

In the following, reference is made to FIG. 9 which shows a further embodiment of a bone plate 1 having a circumferential rib 33, wherein this circumferential rib 33 has a different height in radial direction, therefore towards its symmetry axis which, provided with the reference sign 71, is for example approximately defined by the intersection of plane AA and plane BB.

Figure 9:
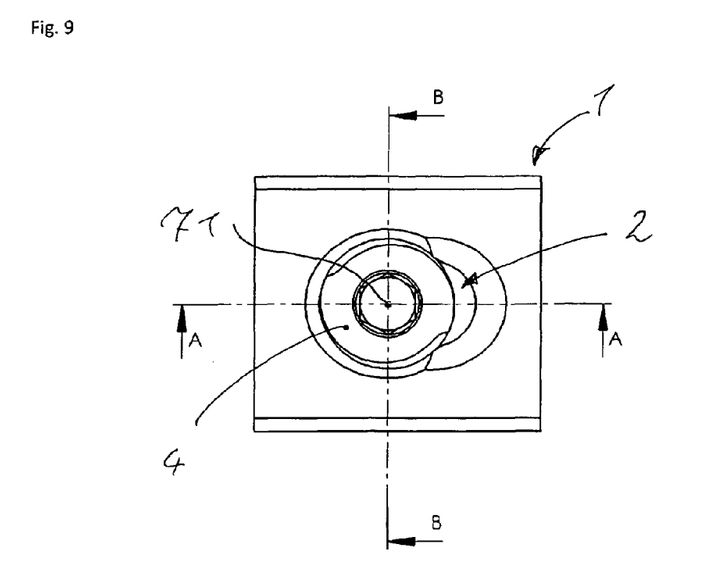
FIG. 9 shows a further embodiment of a bone plate having a circumferential rib with various heights in radial direction.

In FIG. 9, a bone screw 4 is shown inserted into this bone plate 1.

The circumferential rib 33 of the bone plate 1, in this further embodiment, has a wedged cross section with which the height of the wedged cross section in radial direction along one circular, however, is not constant around the circumference of the hole. This means that it does have the same value for each section.

Figures 10, 11:
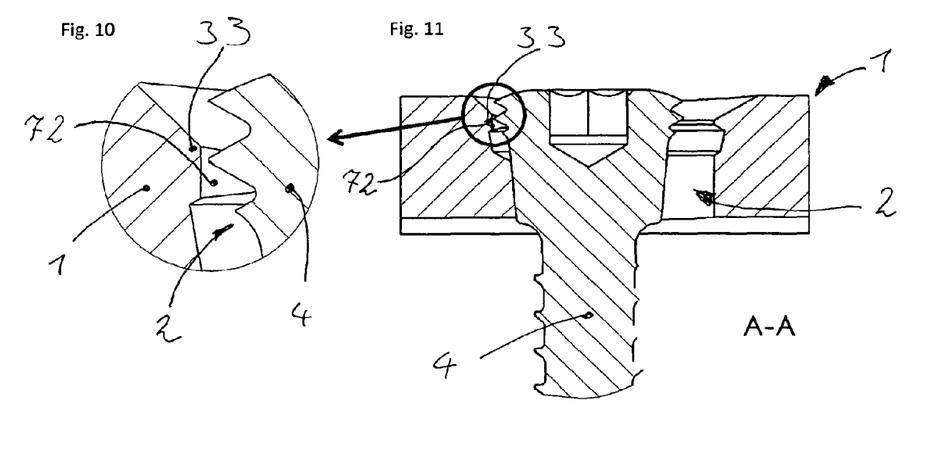
FIG. 10 shows an enlarged sectional view of a part of a sectional drawing along line AA, and therewith extending in parallel to the longitudinal axis of the further embodiment of the bone plate with inserted bone screw, shown in FIG. 9.
FIG. 11 is a sectional drawing along the line AA, and therewith extending in parallel to the longitudinal axis of the further embodiment of the bone plate with inserted bone screw, shown in FIG. 9.

In this further embodiment, the wedged cross section of the circumferential rib 33 is flattened step by step, as it may well be seen in FIG. 10 which shows an enlarged sectional view of a part of a sectional drawing along line AA, and therewith extending in parallel to the longitudinal axis of the further embodiment of the bone plate with inserted bone screw, shown in FIG. 9.

The flattening 72 reduces the radial height in a defined manner so that, with this design, decreased clamping forces are caused by the thread pitch of the thread of the bone screw 4. In the region of the flattening 72, the thread of the bone screw may freely be arranged in front of the circumferential rib 33 what may well be seen also in FIG. 11, with respect to the arrangement of the bone screw 4 relatively to the bone plate 1. Hereby, only an essentially two-sided engagement of the circumferential rib 33 with the thread of the bone screw 4 is caused, as it may be seen in FIGS. 12 and 13, for example.

Figure 12:
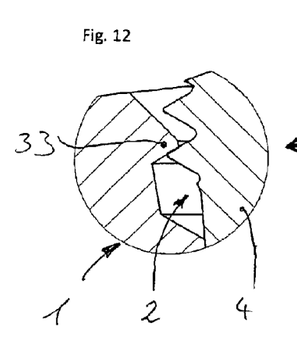
FIG. 12 is an enlarged sectional view of a part of a sectional drawing along the line BB, and therewith extending transversely to the longitudinal axis of the further embodiment of the bone plate with inserted bone screw, shown in FIG. 9.

FIG. 12 shows an enlarged sectional view of a part of the sectional drawing along the line BB, and therewith extending transversely to the longitudinal axis of the further embodiment of the bone plate with inserted bone screw, shown in FIG. 9. This figure makes it easy to see that the left as well as the right side of the thread of the bone screw engages the rib 33. By this design, the slope of the thread of the bone screw may be lowered concerning their friction inhibiting effect, and lower friction forces and self-locking forces may be selectively provided than with a rib 33 having the same radial height.

In this connection, it also is within the scope of the invention that the height in radial direction of the wedged cross section of the circumferential rib 33 essentially is zero, area by area.

Figure 14:
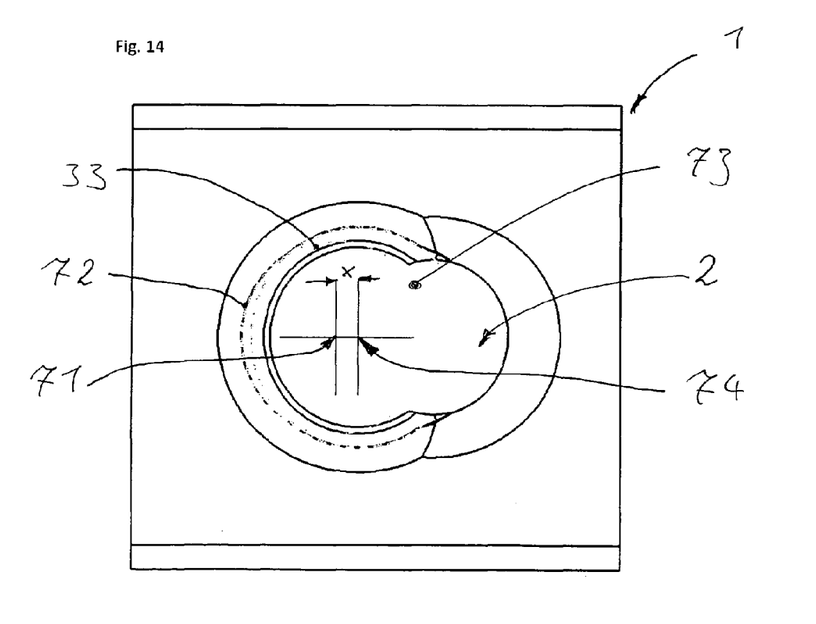
FIG. 14 shows a still further embodiment of the a bone plate having a circumferential rib with different heights in radial direction with which embodiment the symmetry axis of the circumferential rib is arranged offset relatively to the symmetry axis of the conical section of the larger round hole, positioned under the rib, and with which corresponding radii around the respective symmetry axis are dash-dotted, for making their relative displacement easier visible.

In FIG. 14, a still further embodiment of the a bone plate 1 having a circumferential rib 33 with different heights in radial direction is shown with which embodiment the symmetry axis 71 of the circumferential rib is arranged offset relatively to the symmetry axis of the conical section 26 of the larger round hole, positioned under the rib, and with which corresponding radii 72 and 73 around the respective symmetry axis are dash-dotted, for making their relative displacement easier visible.

The circumferential rib 33 may also have the same radial height along the whole circumference, may more or less be brought into engagement with the thread of the head of the bone screw 4, by the displacement.

Here, the circle formed by the radius 72 extends symmetrically to the symmetry axis 71 of the circumferential, radial rib 33, and the circle formed by the radius 73 extends symmetrically to the symmetry axis 74 of the conical section 26 of the larger round hole.

The displacement (referred to by "x" in FIG. 14) between the symmetry axes 73 and 74 defines the change of the radial height of the rib 33.

This displacement is not limited to direction shown in FIG. 14, but may also be arranged in each arbitrary other direction.

If this displacement is equal to, or greater than the radial height of rib 33 in one direction, sections 75 are hereby caused in which the radial height of the wedged cross section of the circumferential rib 33 essentially is zero.

Figure 15:
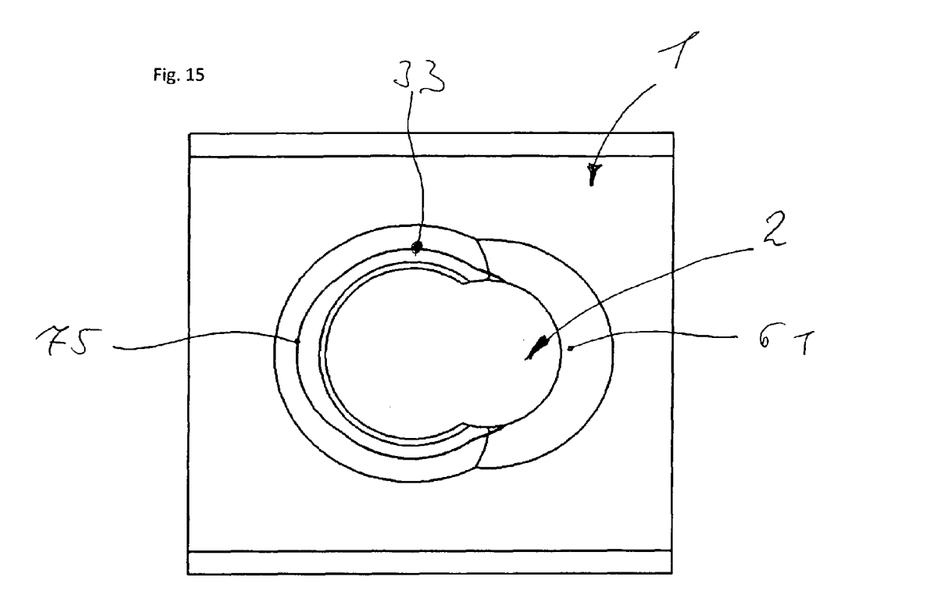
FIG. 15 shows the still further embodiment of the bone plate with circumferential rib with different height in radial direction, shown in FIG. 14, but without the corresponding radii around the respective symmetry axis, for making their real form easier visible.
Figure 16:
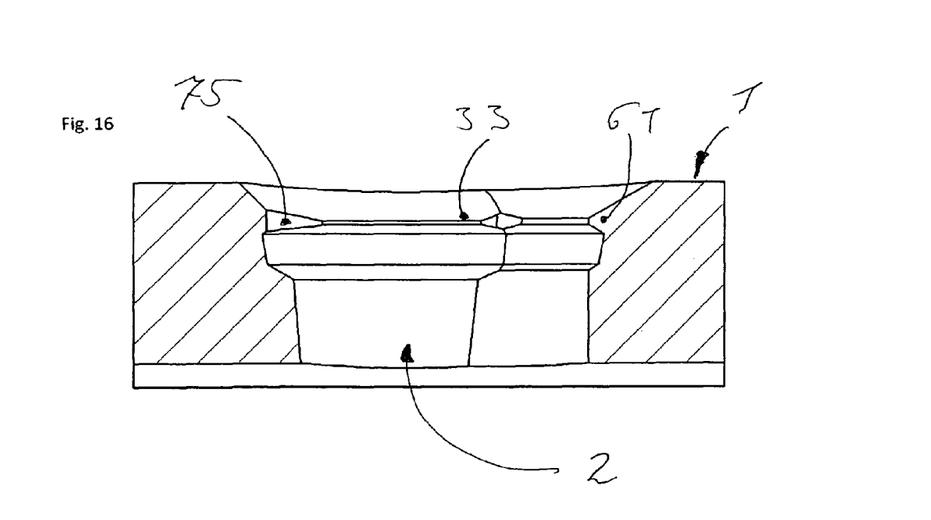
FIG. 16 is a sectional drawing of the still further embodiment shown in FIGS. 14 and 15 along a line which would correspond to the line AA in FIG. 9, and is therefore extending in parallel to the longitudinal axis of the still further embodiment of the bone plate without, however, inserted bone screw, shown in FIGS. 14 and 15.
Figure 17:
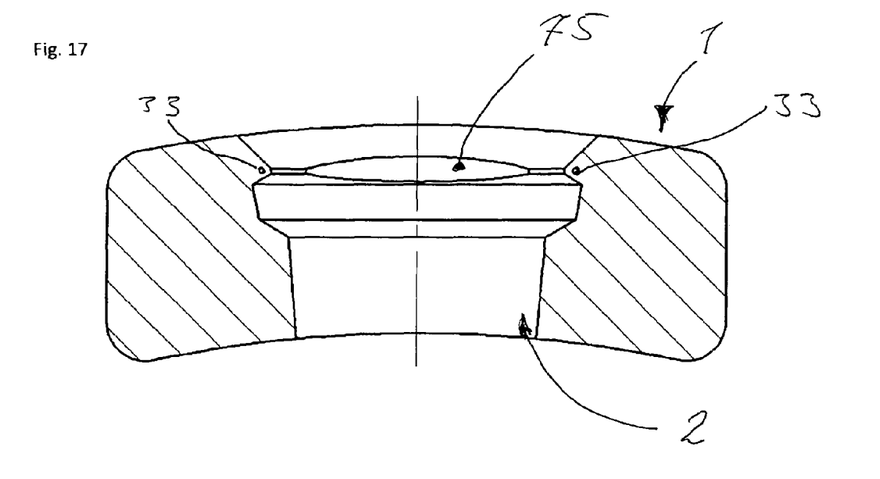
FIG. 17 is a sectional drawing of the still further embodiment shown in FIGS. 14 and 15 along a line which would correspond to the line BB in FIG. 9, and therefore is extending transversely to the longitudinal axis of the still further embodiment of the bone plate without, however, inserted bone screw, shown in FIGS. 14 and 15.

These sections may particularly well be seen in FIGS. 15 to 17.

In this context, FIG. 15 shows the still further embodiment of the bone plate 1 shown in FIG. 14, but without the corresponding radii 72, 73 around the respective symmetry axes 71, 74, for making their real form easier visible.

FIG. 16 shows a sectional drawing of the still further embodiment shown in FIGS. 14 and 15, extending in parallel to the longitudinal axis of the still further embodiment of the bone plate 1 without, however, inserted bone screw 4, shown in FIGS. 14 and 15, for making the course of the rib 33 easier visible.

FIG. 17 shows a sectional drawing of the still further embodiment shown in FIGS. 14 and 15, extending transversely to the longitudinal axis of the still further embodiment of the bone plate 1 however, without, inserted bone screw 4, shown in FIGS. 14 and 15, for making the course of the rib 33 easier visible, also in this case.

As with the embodiment shown in FIGS. 9 to 13, a defined preselectable, decreasing engagement of the thread of the bone screw 4 into the rib 33 is provided as a function of the displacement x. Also in this case, the friction of thread of the bone screw 4 with the rib 33 may be lowered in a defined manner, in comparison with a rib having a constant radial height.

Figure 13:
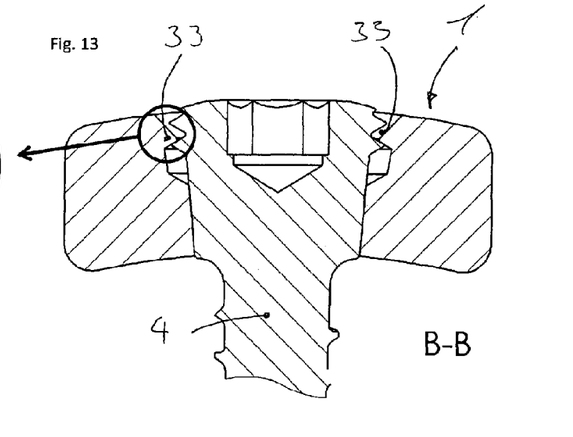
FIG. 13 is a sectional drawing along the line BB, and therewith extending transversely to the longitudinal axis of the further embodiment of the bone plate with inserted bone screw, shown in FIG. 9.

FIG. 17 shows an arrangement with which only a two-sided engagement of the rib 33 into the thread of the bone screw 4 still takes places, essentially similar as shown in FIG. 13.

The circumferential rib 33 may have the effect of an adaptation which counteracts grooving and rupture tendencies at higher stresses, like bending loadings on the bone plate.

In this connection, embodiments with a circumferential rib with which embodiments the radial height of the rib 33 keeps constant are very advantageous with respect to the rigidity and the bending capacity of the bone plate 1.

By means of the invention, a fixation system for bones, having a bone plate and bone screws is created with which embodiment bone screws with a round head may be placed in different oblique angles. Furthermore, the fixation system makes possible the relative shift between the bone fragments to be fixed and the bone plate, when using bone screws. This enables the surgeon to shift bone fragments against each other while fixing the fragments.

What is claimed is:

1. A fixation system for fixing parts of a fractured or damaged bone, the fixation system comprising:
   a bone plate; and
   a bone screw;
   wherein the bone screw comprises a screw shaft and a screw head with a thread and a supporting surface; and
   wherein the bone plate comprises:
      a plate body of rigid material, the plate body defining a plate plane and a longitudinal axis and defining an upper and a lower surface;
      shaped holes extending transversely to the plate plane and consisting of a first hole and a second hole that intersect while forming edges, wherein a smallest diameter of said first hole is greater than a smallest diameter of said second hole;
      one single circumferential radial rib in at least said first hole projecting from a hole wall, leading around said first hole and extending in a plane to a hole centre;
      a bowl-like upper region in at least said second hole above said circumferential radial rib; and
      a truncated lower section in at least said first hole below said circumferential radial rib tapering to the lower surface of the plate body.

2. The fixation system according to claim 1, wherein said supporting surface is conical.

3. The fixation system according to claim 1, wherein said first hole and said second hole are embodied as round holes.

4. The fixation system according to claim 1, wherein said circumferential radial rib leads around said first and said second hole.

5. The fixation system according to claim 1, wherein said supporting surface is placed below said thread of said screw head.

6. The fixation system according to claim 1, wherein the circumferential rib in the first round hole can be clamped with the thread, when the bone screw is inserted into the first round hole.

7. The fixation system according to claim 1, wherein a ridge extends in the first round hole parallel to the radial rib near the upper side of the bone plate, the ridge ending with an edge adjacent to the second round hole.

8. The fixation system according to claim 1, wherein the circumferential radial rib is reduced in the area of the second round hole so as to form an inclined rounded sliding surface and a transitional surface.

9. The fixation system according to claim 1, wherein the circumferential rib forms a leading-in slope within the second round hole, extending to the upper side of the bone plate.

10. The fixation system according to claim 1, wherein the truncated lower section has a smaller diameter than the diameter of the upper region.

11. The fixation system according to claim 1, wherein the upper region of the second round hole includes an upper section having a leading-in slope and a central section having a sloping rounded surface below the plane of the circumferential rib.

12. The fixation system according claim 1, wherein the circumferential rib has a wedge shaped cross-section.

13. The fixation system according to claim 1, wherein the circumferential rib has a wedge shaped cross-section with which the height in radial direction along a perimeter is not constant.

14. The fixation system according to claim 13, including the circumferential rib with different heights in radial direction, wherein the symmetry axis of the circumferential rib is arranged offset relative to a symmetry axis of the conical section of the first hole below the rib.

15. The fixation system according to claim 10, wherein the wedge shaped cross-section of the circumferential rib is flattened in at least one area.

16. The fixation system according to claim 1, wherein said fixation system comprises a further screw with a partial spherical under side of the screw head.

17. A fixation system for fixing parts of a fractured or damaged bone, the fixation system comprising:
   a bone plate; and
   a bone screw;
   wherein the bone screw comprises a screw shaft and a screw head with a supporting surface; and
   wherein the bone plate comprises:
      a plate body of rigid material, the plate body defining a plate plane and a longitudinal axis and defining an upper and a lower surface;
      shaped holes extending transversely to the plate plane and consisting of a first hole and a second hole that intersect while forming edges, wherein a smallest diameter of said first hole is greater than a smallest diameter of said second hole;
      a circumferential radial rib in at least said first hole projecting from a hole wall, leading around said first hole and extending in a plane to a hole centre;
      a upper region with a leading-in slope in at least said second hole above said circumferential radial rib; and
      an inclined lower section in at least said first hole below said circumferential radial rib tapering to the lower surface of the plate body.

18. A bone plate for cooperating with bone screws, the bone plate comprising:
   a plate body of tissue compatible, rigid material, the plate body defining a plate plane and a longitudinal axis and defining an upper an a lower surface;
   shaped holes extending transversely to the plate plane and consisting of a first hole and a second hole that intersect while forming edges, wherein a smallest diameter of said first hole is greater than a smallest diameter of said second hole;
   one single circumferential radial rib in at least said first larger round hole and projecting from a hole wall, leading around said first larger hole;
   an upper region with a leading-in slope in at least said second smaller hole above said circumferential radial rib; and
   an inclined lower section in at least said first larger hole below said circumferential radial rib tapering to the lower surface of the plate body.

* * * * *